United States Patent [19]

Hollenberg et al.

[11] Patent Number: 5,143,722
[45] Date of Patent: Sep. 1, 1992

[54] COSMETIC MAKEUP COMPOSITIONS COMPRISING WATER-IN-OIL EMULSIONS CONTAINING PIGMENT

[75] Inventors: Jane Hollenberg, New York, N.Y.; Lou A. Lombardi, Scotch Plains, N.J.; Marlene Tietjen, New York, N.Y.

[73] Assignee: Revlon, Inc., New York, N.Y.

[21] Appl. No.: 713,496

[22] Filed: Jun. 12, 1991

Related U.S. Application Data

[63] Continuation of Ser. No. 590,603, Sep. 25, 1990, abandoned, which is a continuation of Ser. No. 418,982, Oct. 5, 1989, abandoned, which is a continuation of Ser. No. 203,576, May 26, 1988, abandoned, which is a continuation of Ser. No. 8,997, Dec. 19, 1986, abandoned.

[51] Int. Cl.$^5$ .............................................. A61K 7/021
[52] U.S. Cl. ...................................... 424/63; 424/401; 424/69; 424/59; 424/47; 514/941; 514/938; 514/937; 514/845

[58] Field of Search ............... 424/63, 401, 59; 514/844, 941, 937, 938, 845

[56] References Cited

U.S. PATENT DOCUMENTS

| 4,311,695 | 1/1982 | Starch | 514/63 |
| 4,578,266 | 3/1986 | Tietjen et al. | 424/63 |
| 4,782,095 | 11/1988 | Gum | 514/941 |
| 5,028,417 | 7/1991 | Bhat et al. | 424/63 |
| 5,066,485 | 11/1991 | Brieva et al. | 424/63 |

FOREIGN PATENT DOCUMENTS

2217987A 8/1989 United Kingdom.

*Primary Examiner*—Thurman K. Page
*Assistant Examiner*—D. Colucci
*Attorney, Agent, or Firm*—Julie Blackburn

[57] ABSTRACT

Compositions comprising water-in-oil emulsions are disclosed comprising pigment coated with polysiloxane; a silicone phase; a water phase; and a polydiorganosiloxane-polyoxylalkylene copolymeric surfactant.

15 Claims, No Drawings

COSMETIC MAKEUP COMPOSITIONS COMPRISING WATER-IN-OIL EMULSIONS CONTAINING PIGMENT

This is a continuation of Ser. No. 590,603 filed Sep. 25, 1990, now abandoned, which is a continuation of Ser. No. 07/418,982 filed Oct. 5, 1989, now abandoned, which is continuation of Ser. No. 07/203,576, filed May 26, 1988, now abandoned, which is a continuation of Ser. No. 07/008,997 filed Dec. 19, 1986, now abandoned.

The present invention relates to cosmetic compositions in general and more specifically to compositions of a water™ in-oil emulsion containing other cosmetically desirable components and pigment.

U.S. Pat. No. 4,532,132 discloses certain polyoxyalkylene-substitued siloxanes, and compositions containing said siloxanes and mineral oil. The patent does not, however, suggest how to incorporate high loadings of pigment nor of other siloxane components such as dimethylsiloxane.

U.S. Pat. No. 4,311,695 discloses water-in-oil emulsions useful in the practice of the present invention.

BRIEF SUMMARY OF THE INVENTION

The present invention comprises a cosmetic composition which is a water-in-oil emulsion comprising
(a) an oil phase which comprises
  (i) a coated pigment consisting essentially of finely divided particles of pigment (inorganic or organic) whose surfaces are chemically bonded to, and physically completely coated by, polysiloxane which coating renders the particles hydrophobic, and
  (ii) a silicone component selected from the group consisting of dimethyl polysiloxane having the formula $(CH)_3)_3SiO(Si(CH_3)_2O)_d—Si(CH_3)_3$ wherein the degree of polymerization d is effective to give the fluid a viscosity of 0.65 to one million centistokes at 25° C.; cyclomethicone having a degree of polymerization of 3 to 6; organopolysiloxane having the formula $$X(CH_3)_2SiO—Y—Si(CH_3)_2X$$

wherein X is alkyl or alkoxy having 1 to 30 carbon atoms and Y is a chain of 1 to 100 repeating (Si—O) units containing 1 to 100 units of the formula $(—Si(R_1)(R_2)O—)$ and 0 to 100 units of the formula $(Si(R_3)(R_4)O)$ wherein each of $R_1$, $R_2$, $R_3$ and $R_4$ can be alkyl containing 2 to 30 carbon atoms, phenyl, or phenyl connected to the Si atom by a vinyl group or an alkylene bridge 1 to 3 carbon atoms long; wherein each $R_1$ and $R_3$ can also be —$CH_3$, and each $R_1$ and $R_2$ can also be trimethylsiloxy; and mixtures thereof;
(b) an aqueous phase;
(c) a surfactant which is
a polydiorganosiloxane-polyoxyalkylene copolymer containing at least one polydiorganosiloxane segment consisting of

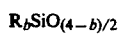

siloxane units wherein b has a value of from 0 to 3 inclusive, there being an average of approximately 2 R radicals per silicon in the copolymer, and R denotes a radical selected from the group consisting of methyl, ethyl, vinyl, phenyl and a divalent radical of 2-6 carbons bonding a polyoxyalkylene segment to the polydiorganosiloxane segment, at least 95 percent of all R radicals being methyl; and containing at least one polyoxyalkylene segment having an average molecular weight of less than 5000 and consisting of from 0 to 50 mol percent polyoxypropylene units and from 50 to 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical;

(d) optionally a second organic surfactant which is silicone-free; and has an HLB value of 2 to 12;

wherein said surfactant component is present in an amount effective to form a stable emulsion of said oil phase in said water phase.

DETAILED DESCRIPTION OF THE INVENTION

The cosmetic compositions of the present invention are useful in a variety of makeup products such as foundations, eyeshadows, blushes, and the like.

The oil phase preferably contains as the major component one or both of dimethyl polysiloxane having the chemical formula (1)

$$(CH_3)_3SiO(Si(CH_3)_2O)_d—Si(CH_3)_3 \qquad (1)$$

in which the degree of polymerization d has a value, typically between 1 and 4160, effective to give the fluid a viscosity of 0.65 to one million centistokes at 25° C.; and/or a cyclomethicone having D=3 to 6 repeating units of formula (1):

$$—(Si(CH_3)_2O)_D— \qquad (2)$$

The dimethyl polysiloxane or cyclomethicone, or the sum when both are present, preferably is up to 95 or even 97 weight percent of the oil phase.

The hydrophobic coated pigments useful in the present invention have one of the following formulas:

$$P—[—O—Si—[—(OSiA_2)_{0-100}—A]_3]_{1-100} \qquad (3)$$

wherein each of the oxygen atoms at the left end of formula (3) is attached to an atom P in the pigment surface; and each A is an alkyl or alkenyl group having up to 30 carbon atoms. A number of adjacent polysiloxane chains as shown in formula (3) can be cross-linked through oxygen atoms to form a polysiloxane chain with up to 100 repeating—Si(—OP)—O—units that extends along the pigment surface, in addition to the polysiloxane chain which extends away from the pigment surface. Examples of alkyl groups are methyl, ethyl, propyl, butyl, pentyl, hexyl, heptyl, octyl, and so forth up to octadecyl. "Alkenyl" includes carbon chains with one or more double bonds; examples of such groups include ethylene, propylene, acrylyl, methacrylyl, and residues of unsaturated fatty acids such as oleic ($C_{17}H_{33}$—), linoleic ($C_{17}H_{31}$—), and linolenic ($C_{17}H_{29}$—).

The coated pigments can also exhibit structural formula (4):

$$P—O—(Si(CH_3)_2O)_p—Si(CH_3)_3 \qquad (4)$$

wherein p is 1-100, and P is an atom in the pigment surface.

The coated pigments can also exhibit structural formula (5):

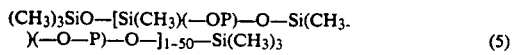  (5)

wherein P is an atom in the pigment surface, and in which each of the up to 100 repeating (Si—O) units is bonded through an oxygen atom to the pigment surface.

The number of polysiloxane chains of formulas (3), (4), and (5) that are bonded to the pigment surface is not known but is sufficiently high to coat the pigment completely and render it completely hydrophobic. Hydrophobicity can readily be determined by placing the coated pigment into water and observing whether any becomes dispersed or suspended in the water.

Suitable pigments include all inorganic and organic pigments or fillers which are usable in cosmetic formulations. Particular examples include talc, mica, titanium dioxide, ferric oxide, ferrous oxide, kaolin, ultramarine, chromium oxide, chromium hydroxide, zinc oxide, silica, manganese violet, and their equivalents. Other examples include lakes of organic colorants such as FD & C Red No. 7 calcium lake, FD & C Yellow No. 5 aluminum lake, D & C Red No. 9 barium lake, and D & C Red No. 30.

The pigment (or a mixture of two or more pigments) can be coated by placing it in dry, finely divided form in a mixer and adding a silicone material selected from the group consisting of (A) $A_1SiX_1X_2X_3$, wherein A is an alkyl or alkenyl group having 1 to 30 carbon atoms, and $X_1$, $X_2$ and $X_3$ are independently chloro, methoxy, or ethoxy (this material will form coated pigment having formula (3));

(B) material of the formula

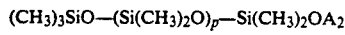

wherein p is 1 to 100, and $A_2$ is hydrogen or an alkyl group having 1 to 30 carbon atoms (this material will form coated pigment having formula (4));

(C) material of the formula

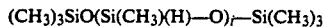

wherein i is 1 to 100 (this material will form coated pigment having formula (5)); or a one-phase mixture of two or all three of A, B, and C. The relative amounts of fluid: pigment should be sufficient to coat the pigment particles. Generally a fluid pigment weight ratio is satisfactory for which 1-4 weight percent of the final product is silicone. The pigment and fluid are intimately mixed thoroughly to obtain a uniform dispersion of the fluid on the pigment, in which the fluid completely coats the particles of pigment. The slurrying operation is advantageously carried out at a temperature of 25° C. to 160° C. effective to promote hydrolysis and reaction of the silicone with the pigment. As an alternative to synthesis, satisfactory coated pigments usable in this invention are commercially available from a variety of sources.

The coated pigment comprises about 2 to about 50 weight percent, and preferably up to about 32 weight percent, of the oil phase.

The oil phase may also contain optional cosmetically acceptable oil-soluble components, such as preservatives, (e.g. up to 0.5 weight percent of the oil phase of paraben such as propyl paraben); up to 1 percent by weight of the oil phase of any conventional cosmetically acceptable fragrance; and one or more of other components well-known to cosmetic chemists, such as those that are intended for cosmetic purposes, for skin-softening and/or for physiological purposes, e.g. for treating skin conditions, like dry skin or chapped skin.

Examples of oil-soluble personal-care components that are useful in the compositions of this invention include, but are not limited to ester waxes, oils and fats of animal or vegetable origin, such as spermaceti wax; beeswax, carnauba wax, lanolin wax, coconut oil, castor oil and lanolin oil; fatty alcohols such as cetyl alcohol, stearyl alcohol and lauryl alcohol; fatty acids such as stearic acid and palmitic acid; alkyl esters of fatty acids such as the methyl, ethyl or isopropyl ester of said fatty acid; hydrocarbon oils and waxes such as mineral oil, petrolatum, perhydrosgualene and paraffin wax; and sunscreens such as octyldimethyl-PABA.

The surfactant must be capable of forming a stable water-in-oil emulsion, which means it will exhibit an HLB value of about 2.5 to about 6. The polydiorganosiloxane segments of the surfactant consist of siloxane units which are interlinked by Si—O—Si linkages and which have the formula

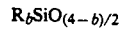

The value of b may range from 0 to 3 for said siloxane units with the provision that there is an average of approximately 2, i.e. from 1.9 to 2.1 R radicals for every silicon atom in the copolymer. Suitable siloxane units thus include $R_3SiO_{1/2}$, $R_2SiO_{2/2}$, $RSiO_{3/2}$, and $SiO_{4/2}$ siloxane units taken is such molar amounts so that b has an average value of approximately 2 in the copolymer. Said siloxane units may be arranged in linear, cyclic and/or branched fashion.

The R radicals of this surfactant may be any radical selected from the group consisting of methyl, ethyl, vinyl, phenyl, and a divalent radical bonding a polyoxyalkylene segment to the polydiorganosiloxane segment. At least 95 percent of all R radicals are methyl radicals; preferably there is a least one methyl radical bonded to each silicon atom in (d). Divalent R radicals preferably contain no more than 6 carbon atoms. Examples of divalent R radicals include —O—, —$C_mH_{2m}O$—, —$C_mH_{2m}$— and —$C_mH_{2m}CO_2$— where m is an integer greater than zero.

Illustrative of the siloxane units that make up the polydiorganosiloxane segments of this first surfactant are the following, where Me denotes methyl and Q denotes said divalent R radical together with its bonded polyoxyalkylene segment: $R_3SiO_{\frac{1}{2}}$ units such as $Me_3SiO_{\frac{1}{2}}$, $Me_2(CH_2=CH)SiO_{\frac{1}{2}}$, $Me_2(C_6H_5)SiO_{\frac{1}{2}}$, $Me(C_6H_5)(CH_2=CH)SiO_{\frac{1}{2}}$, $Me_2(CH_3CH_2)SiO_{\frac{1}{2}}$, $Me_2QSiO_{\frac{1}{2}}$, $MeQ_2SiO_{\frac{1}{2}}$, $Q_3SiO_{\frac{1}{2}}$, $Q_2(CH_3CH_2)SiO_{\frac{1}{2}}$, and $Me(C_6H_5)(Q)SiO_{\frac{1}{2}}$; $R_2SiO_{2/2}$ units such as $Me_2SiO_{2/2}$, $Me(C_6H_5)SiO_{2/2}$, $Me(CH_2=CH)SiO_{2/2}$, $(C_6H_5)_2SiO_{2/2}$, $MeQSiO_{2/2}$, and $Q(C_6H_5)SiO_{2/2}$; $RSiO_{3/2}$ units such as $MeSiO_{3/2}$, $C_6H_5SiO_{3/2}$, $CH_2=CHSiO_{3/2}$, $CH_3CH_2SiO_{3/2}$ and $QSiO_{3/2}$; and $SiO_{4/2}$ units.

It is to be understood that the silicone-based surfactant may comprise one or more of said polydiorganosiloxane segments. The number of and average molecular weight of the polydiorganosiloxane segments in the copolymer is related to the desired weight ratio, hereinafter described, of the polysiloxane and polyoxyalkylene segments in the polymer. Preferably it comprises one polydiorganosiloxane segment having bonded thereto one or more polyoxyalkylene segments.

The polyoxyalkylene segments of this surfactant consist of oxyethylene units of the formula $-CH_2CH_2O-$, alone, or in combination with oxypropylene units of the formula $-CH_2CH(CH_3)O-$, an average of at least half of the oxyalkylene units in the polyoxyalkylene segments being oxyethylene units. Suitable emulsions of this invention are not formed when the polyoxyalkylene segments contain more than 50 mol percent of the relatively hydrophobic oxypropylene unit. The polyoxyalkylene segments thus correspond to the formula $(-CH_2CH_2O-)_p(-CH_2CH(CH_3)O-)_q$ wherein the oxyalkylene units may be arranged in any suitable fashion such as random, alternating and block. The average values of p and q are such that the value of p is equal to, or greater than, the value of q and the sum of p+q is sufficient to provide an average molecular weight of under 5,000.

The polyoxyalkylene segments are bonded to the polydiorganosiloxane segments by at least one terminal portion of said polyoxyalkylene segment, said bonding being by way of a divalent R radical, hereinbefore described. It is to be understood that said bonding may be by both terminal portions of said polyoxyalkylene segment in those copolymers comprising more than one polydiorganosiloxane segments. Any terminal portion of the polyoxyalkylene segment that is not bonded to a polydiorganosiloxane segment is satisfied by a terminating radical. The type of said terminating radical is not critical and may be monovalent, thereby terminating one polyoxyalkylene segment, or polyvalent, thereby terminating more than one polyoxyalkylene segment. Said terminating radicals are made up of atoms selected from the group consisting of carbon, hydrogen, nitrogen and oxygen. Illustrative of said terminating radicals are hydrogen; hydroxyl, alkyl, such as methyl, ethyl, propyl, butyl, benzyl, aryl, such as phenyl; alkoxy such as methoxy, ethoxy, propoxy, butoxy, benzyloxy; aryloxy, such as phenoxy; alkenyloxy, such as vinyloxy and allyloxy; acyloxy, such as phenoxy; alkenyloxy, such as vinyloxy and allyloxy; acyloxy, such as acetoxy, acryloxy and propionoxy and amino such as dimethylamino.

Herein "copolymer" means either a block arrangement of segments such as denoted by the formulae $(AB)_c$, $A(BA)_c$ and $B(AB)_c$ or a pendant arrangement of segments such as $(AB_d)_c$ or combinations thereof wherein A denotes a polydiorganosiloxane segment, B denotes a polyoxyalkylene segment and c and d denote integers greater than zero and greater than one, respectively. Copolymers (d) may be prepared by modification of the well-known methods described in the polydiorganosiloxane-polyoxyalkylene copolymer art. The following patents are hereby incorporated herein by reference to show the preparation of polydiorganosiloxane-polyoxyalkylene copolymers Haluska, U.S. Pat. No. 2,868,824; Haluska, U.S. Pat. No. Re. 25,727; Bailey, U.S. Pat. No. 3,172,899; Pater, U.S. Pat No. 3,234,252, Simmler, et al. U.S. Pat. No. 3,174,987; Bailey, et al., U.S. Pat Nos. 3,562,786, 3,600,418 and 3,629,308; Holdstock, U.S. Pat. No. 3,629,165; and Gee et al., U.S. Pat. No. 4,122,029.

It is to be understood that the silicon-bonded reaction groups such as silicon-bonded hydrogen for addition reactions or silicon-bonded hydrolyzable radicals for displacement reactions are preferably completely reacted in the copolymer preparation process, but that trace amounts of said reaction groups may escape reaction with the polyoxyalkylene and may be found in the surfactant.

Non-essential components which are common to personal-care compositions of the art, such as perfumes, humectants, preservatives, colorants and electrolytes may be incorporated into the compositions of this invention provided they do not destablize the emulsion so as to cause a breaking or an inverting of the emulsion.

The cosmetic composition of the present invention can optionally further comprise a second surfactant which is organic, silicone-free, and has an HLB value of 2 to 12, provided that the overall effective HLB value still permits formation of the desired water-in-oil emulsion. The amount should be about 0.25 to 2 weight percent of the composition, and preferably 0.5 to 1 weight percent thereof. As is well known to those of ordinary skill in this art, the HLB value is determined by a standardized technique for measuring the solubility of a surfactant. Said surfactant may be anionic, cationic or non-ionic with respect to its hydrophilic portion. Satisfactory surfactants useful in this invention include polyoxyalkylene ethers, such as the "Laureth" family of compounds having the general formula $CH_3(CH_2)_{10}CH_2(OCH_2CH_2)_nOH$ in which n has an average value of 3–15 and preferably 5–10. Other examples of suitable surfactants include sodium capryl lactylate and sodium stearoyl lactylate as anionic surfactants, quaternary ammonium chlorides manufactured by Tomah Products, Inc. as Emulsifier Three (TM) and Emulsifier Four (TM) as coationic surfactants and polyethylene glycol (200) monolaurate, olycerol monolaurate, N,N-dimethylcaproamide, diethylene glycol monolaurate, sorbitan monolaurate and nonylphenoxy polyethoxyethanol as non-ionic surfactants. Other satisfactory silicone-free surfactants include the following glyceryl monooleate, polyglyceryl-4 decaoleate, PEG-8 Oleate, PEG-4 lauryl ether, PEG-9 lauryl ether and sorbitan sesquioleate. Other examples of suitable organic surfactants having an HLB value of from 2 to 12 may be found by reference to standard publications such as McCutcheon's, Detergents and Emulsifiers, Allred Publishing Company, Ridgewood, N.J. (1974).

The water phase of the composition of the present invention may be simply water, or may contain water-soluble cosmetically acceptable components provided that the emulsion is not destabilized or inverted therein. Examples include humectants, including propylene glycol, glycerine, sodium pyrrolidone carboxylic acids, citric acid, lactic acid and derivatives thereof; preservatives, such as methyl paraben; electrolytes, such as NaCl and magnesium sulfate; and sunscreens such as TEA-salicylate or PABA. The water phase comprises up to about 80 weight percent, and preferably up to about 60 weight percent, of the composition, and at least about 15 weight percent of the composition.

The composition can also contain effective amounts of optional cosmetically acceptable thickeners or other components such as cellulose derivatives, organically modified clays, and organic thickeners to achieve desired properties such as viscosity, stability or afterfeel. Specific examples of such components are well-known to cosmetic chemists. Some examples are the following: hydroxyethyl cellulose, xanthan gum, cationic cellulosic resins, quaternium-18 hectorite, and glyceryl trihydroxy stearate.

To make the composition of the present invention, one simply (1) stirs thoroughly together all the components of the oil phase and the surfactant(s), (2) disperses the hydrophobic pigments in the oil phase utilizing a high speed disperser or high shear mill and then (3) stirs in the water phase including any components dissolved in the water phase. Any standard high speed stirring or homogenizing apparatus known to the art can be used to carry out the mixing operation.

The invention will be described further in the following examples, which should be interpreted as illustrative rather than limiting.

EXAMPLE 1

A cream foundation was made by thoroughly mixing together the following components.

| Component | Amount (% by weight) |
|---|---|
| Cyclomethicone (80% D = 4; 20% D = 5) | 22.6 |
| Surfactant (Dow Corning 3225-C silicone/glycol fluid) | 16.0 |
| Laureth-7 (formula (7) wherein n = 7) | 0.5 |
| Propyl paraben | 0.1 |
| Bentone gellant | 5.0 |
| Pigment: | |
| Red Iron Oxide | 0.9 |
| Yellow Iron Oxide | 2.0 |
| Black Iron Oxide | 0.2 |
| Talc | 4.5 |
| $TiO_2$ | 12.0 |
| Water | 26.0 |
| Sodium Chloride | 2.0 |
| Propylene Glycol | 8.0 |
| Methylparaben | 0.2 |

The pigment comprised an intimate blend of the five indicated components, all of which had been thoroughly coated with a polymethyl hydrogen siloxane coating bonded to the pigment surface.

EXAMPLE 2

A liquid foundation was prepared by mixing together in the manner indicated above the following components:

| Components | Amount (% by weight) |
|---|---|
| Cyclomethicone (D = 4) | 12.00 |
| Dimethicone (viscosity 10 cs) | 5.00 |
| Surfactant (Dow Corning 3225-C fluid) | 20.00 |
| Laureth-9 | 0.50 |
| Propyl Paraben | 0.10 |
| Pigment* | |
| Red Iron Oxide | 0.70 |
| Yellow Iron Oxide | 1.50 |
| Black Iron Oxide | 0.20 |
| Talc | 3.30 |
| $TiO_2$ | 8.50 |
| Water | 38.00 |
| Sodium Chloride | 2.00 |
| Propylene Glycol | 8.00 |
| Methyl Paraben | 0.20 |

*Pigment was coated with polymethyl hydrogen siloxane.

EXAMPLE 3

An eyeshadow was prepared by mixing together in the manner indicated above the following components:

| Component | Amount (% by weight) |
|---|---|
| Cyclomethicone (D = 4) | 2.00 |
| Dimethicone (viscosity = 10 cs) | 5.00 |
| Surfactant (Dow Corning 3225-C fluid) | 20.00 |
| PEG-7 $C_{12-15}$ ether | 0.50 |
| Propyl Paraben | 0.10 |
| Pigment* | |
| Chromium oxide | 6.20 |
| Ultramarine blue | 4.00 |
| $TiO_2$ coated mica (Mearl Superpearl 100) | 6.00 |
| Water | 46.00 |
| Sodium Chloride | 2.00 |
| Propylene Glycol | 8.00 |
| Methyl Paraben | 0.20 |

*The pigment was coated with methyl trimethoxy silane to form a coating of polydimethyl siloxane.

EXAMPLE 4

An eyeliner was prepared by mixing together in the manner indicated above the following components:

| Component | Amount (% by weight) |
|---|---|
| Cyclomethicone (D = 4) | 13.20 |
| Surfactant (Dow Corning 3225-C fluid) | 16.00 |
| Polyglyceryl-4 oleate | 0.50 |
| Pigment* | |
| Black and Red Iron Oxides | 10.00 |
| Talc | 4.00 |
| Water | 46.00 |
| Sodium Chloride | 2.00 |
| Propylene Glycol | 8.00 |
| Methyl Paraben | 0.20 |

*Pigment was coated with polymethylhydrogen siloxane and mineral oil.

EXAMPLE 5

A blusher was prepared by mixing together in the manner indicated above the following components:

| Component | Amount (% by weight) |
|---|---|
| Cyclomethicone (D = 4) | 8.00 |
| Dimethicone | 3.00 |
| Silsoft MG (Union Carbide) | 18.00 |
| Laureth - 9 | 0.50 |
| Propyl Paraben | 0.10 |
| Pigment* | |
| D & C Red #7 Ca Lake | 1.00 |
| FD & C Yellow #5 Al Lake | 0.50 |
| Red Iron Oxide | 0.80 |
| Titanium Dioxide | 2.00 |
| Talc | 9.70 |
| Water | 46.00 |
| Dow Corning 193 fluid | 0.20 |
| Sodium Chloride | 2.00 |
| Propylene Glycol | 8.00 |
| Methyl Paraben | 0.20 |

*pigment was coated with polymethyl hydrogen siloxane

EXAMPLE 6

A liquid foundation was prepared by mixing together in the manner indicated above the following

| Component | Amount (% by weight) |
|---|---|
| Cyclomethicone (D = 4) | 12.00 |
| Surfactant (Dow Corning 3225-C fluid) | 20.00 |

-continued

| Component | Amount (% by weight) |
|---|---|
| Phenyl Trimethicone (Dow Corning 556 fluid) | 5.00 |
| Laureth - 9 | 0.50 |
| Propyl Paraben | 0.10 |
| Pigment* | |
| Red Iron Oxide | 0.90 |
| Yellow Iron Oxide | 1.75 |
| Black Iron Oxide | 0.22 |
| Talc | 3.33 |
| TiO$_2$ | 8.00 |
| Water | 39.00 |
| Sodium Chloride | 1.00 |
| Glycerine | 8.00 |
| Methyl Paraben | 0.20 |

*pigment was coated with polymethyl hydrogen siloxane.

What is claimed is:

1. A cosmetic make-up composition which is a water-in-oil emulsion comprising
   a) an oil phase which comprises
      i) About 2 to 50% by weight of the oil phase of a coated pigment consisting essentially of finely divided particles of pigment whose surfaces are chemically bonded to, and physically completely coated by, polysiloxane which coating renders the particles hydrophobic, and
      ii) up to about 97% by weight of the oil phase of a silicone component selected from the group consisting of dimethyl polysiloxane having the formula (CH$_3$)$_3$SiO(Si(CH$_3$)$_2$O)$_d$—Si(CH$_3$)$_3$ wherein the degree of polymerization d is effective to give the fluid a viscosity of 0.65 to one million centistokes at 25° C.; cyclomethicone having a degree of polymerizaton of 3 to 6; organopolysilioxane having the formula:

$$X(CH_3)_2SiO-Y-Si(CH_3)_2X$$

wherein X is alkyl or alkoxy having 1 to 30 carbon atoms and Y is a chain of 1 to 100 repeating (Si—O) units containing 1 to 100 units of the formula (—Si(R$_1$)(R$_2$)O—) and 0 to 100 units of the formula (Si(R$_3$)(R$_4$)O) wherein each of R$_1$, R$_2$, R$_3$ and R$_4$ can be alkyl containing 2 to 30 carbon atoms, phenyl, or phenyl connected to the Si atom by a vinyl group or an alkylene bridge 1 to 3 carbon atoms long; wherein each R$_1$ and R$_3$ can also be —CH$_3$, and each R$_1$ and R$_2$ can also be trimethylsiloxy; and mixtures thereof;
   b) 15 to 60% by weight of the total composition of an aqueous phase;
   c) a surfactant which is a polydiorganosiloxane-polyoxyalkylene copolymer containing at least one polydiorganosiloxane segment consisting of $$R_b SiO_{(4-b)/2}$$

siloxane units wherein b has a value of from 0 to 3 inclusive, there being an average of approximately 2 R radicals per silicon in the copolymer, and R denotes a radical selected from the group consisting of methyl, ethyl, vinyl, phenyl and a divalent radical bonding a polyoxyalkylene segment to the polydiorganosiloxane segment, at least 95 percent of all R radicals being methyl; and containing at least one polyoxalkylene segment having an average molecular weight of less than 5000 and consisting of from 0 to 50 mol percent polyoxypropylene units and from 50 to 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical;
   d) and further comprising a silicone-free surfactant having an HLB of 2-12;
   wherein said surfactants are present in a combined amount effective to form a stable emulsion of said water phase in said oil phase.

2. A composition according to claim 1 wherein the pigment is one or more substances selected from the group consisting of talc, mica, titanium dioxide, ferric oxide, ferrous oxide, kaolin, ultramarine, chromium oxide, chromium hydroxide, zinc oxide, silica, manganese violet.

3. A composition according to claim 1 further comprising a cosmetically acceptable component dissolved in the oil phase.

4. A composition according to claim 1 further comprising a cosmetically acceptable component dissolved in the aqueous phase.

5. A cosmetic make up composition which is a water-in-oil emulsion comprising
   (a) an oil phase which comprises
      (i) about 2-50% by weight of the oil phase of a coated pigment consisting essentially of finely divided particles of talc, mica, titanium dioxide, ferric oxide, ferrous oxide, kaolin, ultramarine, chromium oxide, chromium hydroxide, zinc oxide, silica, manganese violet, organic pigments, or mixtures thereof; whose surfaces are chemically bonded to and physically completely coated by a polysiloxane selected from the group consisting of polymethyl hydrogen siloxane and mineral oil, polydimethylsiloxane, methyltrimethyoxysilane, polymethyl hydrogen siloxane, or mixtures thereof, which coating renders the particles hydrophobic;
      (ii) up to about 97% by weight of the oil phase of a silicone component selected from the group consisting of cyclomethicone, dimethicone, phenyltrimethicone, or mixtures thereof,
   (b) about 15-60% of an aqueous phase;
   (c) a surfactant selected from the group consisting of cyclomethicone, dimethicone copolyol, or mixtures thereof,
   wherein said surfactant component is present in an amount effective to form a stable emulsion of said water phase in said oil phase.

6. The composition of claim 5 further comprising about 0.25-2% by weight of the total composition of a silicone free surfactant having an HLB of 2-12.

7. The composition of claim 6 wherein the silicone free surfactant is selected from the group consisting of Laureth-7, Laureth-9, PEG-7 C$_{12-15}$ ether, polyglyceryl-4 oleate, or mixtures thereof.

8. The composition of claim 6 wherein the silicone oil phase additionally comprises ester waxes, oils, fats, fatty alcohols, fatty acids, hydrocarbon oils, waxes, sunscreens, preservatives fragrances or mixtures thereof.

9. The composition of claim 6 wherein the aqueous phase additionally comprises humectants, preservatives, electrolytes, sunscreens, or mixtures thereof.

10. The composition of claim 6 having the formula

|  | w/w % |
|---|---|
| cyclomethicone (80% D = 4, 20% D = 5) | 22.6 |
| surfactant (cyclomethicone and dimethicone copolyol) | 16.0 |
| Laureth-7 | 0.5 |
| Propyl paraben | 0.1 |
| Bentone gellant | 5.0 |
| Pigment: | |
| Red iron oxide | 0.9 |
| Yellow iron oxide | 2.0 |
| Black iron oxide | 0.2 |
| Talc | 4.5 |
| Titanium dioxide | 12.0 |
| Water | 26.0 |
| Sodium chloride | 2.0 |
| Propylene glycol | 8.0 |
| Methyl paraben | 0.2. |

11. The composition of claim 6 having the formula

|  | w/w % |
|---|---|
| cyclomethicone (D = 4) | 12.00 |
| Dimethicone (viscosity 10 cs) | 5.00 |
| Surfactant (cyclomethicone and dimethicone copolyol) | 20.00 |
| Laureth-9 | 0.5 |
| Propyl paraben | 0.10 |
| Pigment | |
| Red iron oxide | 0.70 |
| Yellow iron oxide | 1.50 |
| Black iron oxide | 0.20 |
| Talc | 3.30 |
| Titanium dioxide | 8.50 |
| Water | 38.00 |
| Sodium chloride | 2.00 |
| Propylene glycol | 8.00 |
| Methyl paraben | 0.20. |

12. The composition of claim 6 having the formula

|  | w/w % |
|---|---|
| cyclomethicone (D = 4) | 2.00 |
| Dimethicone (viscosity 10 cs) | 5.00 |
| Surfactant (cyclomethicone and dimethicone copolyol) | 20.00 |
| PEG-7 $C_{12-15}$ ether | 0.50 |
| Propyl paraben | 0.10 |
| Pigment | |
| chromium oxide | 6.20 |
| ultramarine blue | 4.00 |
| titanium dioxide coated mica | 6.00 |
| Water | 46.00 |
| Sodium chloride | 2.00 |
| Propylene glycol | 8.00 |
| Methyl paraben | 0.20. |

13. The composition of claim 6 having the formula

|  | w/w % |
|---|---|
| cyclomethicone (D = 4) | 13.20 |
| Surfactant (cyclomethicone and dimethicone copolyol) | 16.00 |
| Polyglyceryl 4-oleate | 0.50 |
| Pigment | |
| Black and red iron oxides | 10.00 |
| Talc | 4.00 |
| Water | 46.00 |
| Sodium chloride | 2.00 |
| Propylene glycol | 8.00 |
| Methyl paraben | 0.20. |

14. The composition of claim 6 having the formula

|  | w/w % |
|---|---|
| cyclomethicone (D = 4) | 8.00 |
| Dimethicone | 3.00 |
| Surfactant (cyclomethicone and dimethicone copolyol) | 18.00 |
| Laureth-9 | 0.50 |
| Propyl paraben | 0.10 |
| Pigment | |
| D & C Red #7 Ca Lake | 1.00 |
| FD & C Yellow #5 Al Lake | 0.50 |
| Red iron oxide | 0.80 |
| Titanium dioxide | 2.00 |
| Talc | 9.70 |
| Water | 46.00 |
| Dimethicone copolyol | 0.20 |
| Sodium chloride | 2.00 |
| Propylene glycol | 8.00 |
| Methyl paraben | 0.20. |

15. The composition of claim 6 having the formula

|  | w/w % |
|---|---|
| Cyclomethicone | 12.00 |
| Surfactant (cyclomethicone and dimethicone copolyol) | 20.00 |
| Phenyltrimethicone | 5.00 |
| Laureth-9 | 0.50 |
| Propyl paraben | 0.10 |
| Pigment | |
| Red iron oxide | 0.90 |
| Yellow iron oxide | 1.75 |
| Black iron oxide | 0.22 |
| Talc | 3.33 |
| Titanium dioxide | 8.00 |
| Water | 39.00 |
| Sodium chloride | 1.00 |
| Glycerine | 8.00 |
| Methyl paraben | 0.20. |

* * * * *

UNITED STATES PATENT AND TRADEMARK OFFICE
CERTIFICATE OF CORRECTION

PATENT NO. : B1 5,143,722  
DATED : August 24, 1999  
INVENTOR(S) : Hollenberg et al.

Page 1 of 2

It is certified that error appears in the above-identified patent and that said Letters Patent is hereby corrected as shown below:

ON THE TITLE PAGE:

[73] Assignee:
    "Chemical Bank, New York, N.Y." should read --Revlon Consumer Products Corporation, New York, N.Y.--.

[63] Related U.S. Application Data:
    Line 3, after "abandoned," --which is a continuation of application No. 08/203,576, May 26, 1988, abandoned,-- should be inserted.

COLUMN 2:
    Line 37, "oxsilane]" should read --oxysilane]--.

COLUMN 3;
    Line 30, "5.00" should read --20.00--.
    Line 43, "by" should read --by,--.
    Line 50, "22.6" should read --2.00--.

UNITED STATES PATENT AND TRADEMARK OFFICE
CERTIFICATE OF CORRECTION

PATENT NO. : B1 5,143,722
DATED : August 24, 1999
INVENTOR(S) : Hollenberg et al.

It is certified that error appears in the above-identified patent and that said Letters Patent is hereby corrected as shown below:

<u>COLUMN 4</u>:
 Line 48, "cyclomethicone (D=4)" should read --Cyclomethicone--.

Signed and Sealed this

Sixteenth Day of May, 2000

*Attest:*

Q. TODD DICKINSON

*Attesting Officer*    *Director of Patents and Trademarks*

REEXAMINATION CERTIFICATE (3844th)

United States Patent [19]
Hollenberg et al.

[11] B1 5,143,722
[45] Certificate Issued Aug. 24, 1999

[54] COSMETIC MAKEUP COMPOSITIONS COMPRISING WATER-IN-OIL EMULSIONS CONTAINING PIGMENT

[75] Inventors: Jane Hollenberg, New York, N.Y.; Lou A. Lombardi, Scotch Plains, N.J.; Marlene Tietjen, New York, N.Y.

[73] Assignee: Chemical Bank, New York, N.Y.

Reexamination Request:
No. 90/004,938, Mar. 12, 1998

Reexamination Certificate for:
Patent No.: 5,143,722
Issued: Sep. 1, 1992
Appl. No.: 08/713,496
Filed: Jun. 12, 1991

Related U.S. Application Data

[63] Continuation of application No. 08/590,603, Sep. 25, 1990, abandoned, which is a continuation of application No. 08/418,982, Oct. 5, 1989, abandoned, which is a continuation of application No. 08/008,997, Dec. 19, 1986, abandoned.

[51] Int. Cl.$^6$ ................................................ A61K 7/021
[52] U.S. Cl. .................. 424/63; 424/47; 424/59; 424/69; 424/401; 514/845; 514/937; 514/938; 514/941
[58] Field of Search .................. 424/63, 401, 69, 424/59, 47; 514/941, 938, 937, 845

[56] References Cited

U.S. PATENT DOCUMENTS

| | | | |
|---|---|---|---|
| 4,122,029 | 10/1978 | Gee et al. | 252/309 |
| 4,311,695 | 1/1982 | Starch | 424/184 |
| 4,532,132 | 7/1985 | Keil | 514/772 |

FOREIGN PATENT DOCUMENTS 0 133 963 A2   3/1985   European Pat. Off. .

*Primary Examiner*—Jyothsna Venkat

[57] ABSTRACT

Compositions comprising water-in-oil emulsions are disclosed comprising pigment coated with polysiloxane; a silicone phase; a water phase; and a polydiorganosiloxane-polyoxylalkylene copolymeric surfactant.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, paragraph 3:
wherein said surfactant component is present in an amount effective to form a stable emulsion of [said oil phase in said water phase] *said water phase in said oil phase*.

AS A RESULT OF REEXAMINATION, IT HAS BEEN DETERMINED THAT:

The patentability of claims 3 and 4 is confirmed.
Claim 6 is cancelled.
Claims 1–2, 5 and 7–15 are determined to be patentable as amended.

1. A cosmetic make-up composition which is a water-in-oil emulsion comprising
   a) an oil phase which comprises
      i) about 2 to 50% by weight of the oil phase of a coated pigment consisting essentially of finely divided particles of pigment whose surfaces are chemically bonded to, and physically completely coated by, polysiloxane which coating renders the particles hydrophobic, and
      ii) up to about 97% by weight of the oil phase of a silicone component selected from the group consisting of dimethyl polysiloxane having the formula

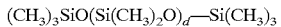

$(CH_3)_3SiO(Si(CH_3)_2O)_d\text{—}Si(CH_3)_3$ wherein the degree of polymerization d is effective to give the fluid a viscosity of 0.65 to one million centistokes at 25° C.; cyclomethicone having a degree of polymerization of 3 to 6; organopolysilioxane having the formula:

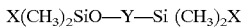

$X(CH_3)_2SiO\text{—}Y\text{—}Si\,(CH_3)_2X$ wherein X is alkyl or alkoxy having 1 to 30 carbon atoms and Y is a chain of 1 to 100 repeating (Si—O) units containing 1 to 100 units of the formula (—Si($R_1$)($R_2$)O—) and 0 to 100 units of the formula (Si($R_3$)($R_4$)O) wherein each of $R_1$, $R_2$, $R_3$ and $R_4$ can be alkyl [containing] *having* 2 to 30 carbon atoms, phenyl, or phenyl connected to the Si atom by a vinyl group or an alkylene bridge 1 to 3 carbon atoms long; wherein each $R_1$ and $R_3$ can also be —$CH_3$, and each $R_1$ and $R_2$ can also be trimethylsiloxy; and mixtures thereof;
   b) 15 to 60% by weight of the total composition of an aqueous phase;
   c) a surfactant which is polydiorganosiloxane-polyoxyalkylene copolymer containing at least one polydiorganosiloxane segment consisting of

$R_bSiO_{(4-b)/2}$ siloxane units wherein b has a value of from 0 to 3 inclusive, there being an average of approximately 2 R radicals per silicon in the copolymer, and R denotes a radical selected from the group consisting of methyl, ethyl, vinyl, phenyl and a divalent radical bonding a polyoxyalkylene segment to the polydiorganosiloxane segment, at least 95 percent of all R radicals being methyl; and containing at least one polyoxyalkylene segment having an average molecular weight of less than 5000 and consisting of from 0 to 50 mol percent polyoxypropylene units and from 50 to 100 mol percent polyoxyethylene units, at least one terminal portion of said polyoxyalkylene segment being bonded so said polydiorganosiloxane segment, any terminal portion of said polyoxyalkylene segment not bonded to said polydiroganosiloxane segment being satisfied by a terminating radical;
   d) *and further comprising a silicone-free surfactant having an HLB of 2–12;*
wherein said *surfactants are* present in a combined amount effective to form a stable emulsion of said water phase in said oil phase.

2. A composition according to claim 1 wherein the pigment is one or more substances selected from the group consisting of talc, mica, titanium dioxide, ferric oxide, ferrous oxide, kaolin, ultramarine, chromium oxide, chromium hydroxide, zinc oxide, silica, *and* manganese violet.

5. *A cosmetic make up composition which is a water-in-oil emulsion comprising*
   (a) *an oil phase which comprises*
      (i) *about 2–50% by weight of the oil phase of a coated pigment consisting essentially of finely divided particles of pigment, wherein the pigment is selected from the group consisting of* talc, mica, titanium dioxide, ferric oxide, ferrous oxide, kaolin, ultramarine, chromium oxide, chromium hydroxide, zinc oxide, silica, manganese violet, *organic pigments,* [or] *and* mixtures thereof; whose surfaces are chemically bonded to and physically completely coated by a polysiloxane selected from the group consisting of polymethyl hydrogen siloxane and mineral oil, polydimethylsiloxane, [methyltrimethyoxsilane] *methyltrimethoxysilane,* polymethyl hydrogen siloxane, [or] *and* mixtures thereof, which coating renders the particles hydrophobic; *and*
      (ii) up to about 97% by weight of the oil phase of a silicone component selected from the group consisting of cyclomethicone, dimethicone, phenyltrimethicone, [or] *and* mixtures thereof, *said silicone component comprising at least cyclomethicone;*
   (b) about 15–60% of an aqueous phase;
   (c) *dimethicone copolyol surfactant; and*
   (d) *about 0.25–2% by weight of the total composition of a silicone-free surfactant having an HLB of 2–12;*
   [(c) a surfactant selected from the group consisting of cyclomethicone, dimethicone copolyol, or mixtures thereof,]
wherein said [surfactant component is] *surfactants are* present in [an] *a combined* amount effective to form a stable emulsion of said water phase in said oil phase.

7. The composition of claim [6] *5* wherein the silicone free surfactant is selected from the group consisting of Laureth-7, Laureth-9, PEG-7 $C_{12-15}$ ether, polyglyceryl-4 oleate, [or] *and* mixtures thereof.

8. The composition of claim [6] *5* wherein the silicone oil phase additionally comprises ester waxes, oils, fats, fatty alcohols, fatty acids, hydrocarbon oils, waxes, sunscreens, preservatives, fragrances or mixtures thereof.

9. The composition of claim [6] *5* wherein the aqueous phase additionally comprises humectants, preservatives, electrolytes, sunscreens, or mixtures thereof.

10. [The composition of claim 6] *A cosmetic foundation that is a water-in-oil emulsion* having the formula

| | w/w % |
|---|---|
| cyclomethicone (80% D = 4, 20% D = 5) | 22.6 |
| surfactant (cyclomethicone and dimethicone copolyol) | 16.0 |
| Laureth-7 | 0.5 |
| Propyl paraben | 0.1 |
| Bentone gellant | 5.0 |
| Pigment: | |
| Red iron oxide | 0.9 |
| Yellow iron oxide | 2.0 |
| Black iron oxide | 0.2 |
| Talc | 4.5 |
| Titanium dioxide | 12.0 |
| Water | 26.0 |
| Sodium chloride | 2.0 |
| Propylene glycol | 8.0 |
| Methyl paraben | 0.2 |

*wherein the surfaces of the particles of pigment are chemically bonded to, and physically completely coated by, polymethyl hydrogen siloxane.*

11. [The composition of claim 6] *A cosmetic foundation that is a water-in-oil emulsion* having the formula

| | w/w % |
|---|---|
| cyclomethicone (D = 4) | 12.00 |
| Dimethicone (viscosity 10 cs) | 5.00 |
| Surfactant (cyclomethicone and dimethicone copolyol) | 5.00 |
| Laureth-9 | 0.5 |
| Propyl paraben | 0.10 |
| Pigment: | |
| Red iron oxide | 0.70 |
| Yellow iron oxide | 1.50 |
| Black iron oxide | 0.20 |
| Talc | 3.30 |
| Titanium dioxide | 8.50 |
| Water | 38.00 |
| Sodium chloride | 2.00 |
| Propylene glycol | 8.00 |
| Methyl paraben | 0.20 |

*wherein the surfaces of the particles of pigment are chemically bonded to, and physically completely coated by polymethyl hydrogen siloxane.*

12 [The composition of claim 6] *An eyeshadow that is a water-in-oil emulsion* having the formula

| | w/w % |
|---|---|
| cyclomethicone (D = 4) | 22.6 |
| Dimethicone (viscosity 10 cs) | 5.00 |
| Surfactant (cyclomethicone and dimethicone copolyol) | 20.00 |
| PEG-7 $C_{12-15}$ ether | 0.50 |
| Propyl paraben | 0.10 |
| Pigment: | |
| chromium oxide | 6.20 |
| ultramarine blue | 4.00 |
| titanium dioxide coated mica | 6.00 |
| Water | 46.00 |
| Sodium chloride | 2.00 |
| Propylene glycol | 8.00 |
| Methyl paraben | 0.20 |

*wherein the surfaces of the particles of pigment are chemically bonded to, and physically completely coated by, polydimethyl siloxane.*

13. [The composition of claim 6] *An eyeliner that is a water-in-oil emulsion* having the formula

| | w/w % |
|---|---|
| cyclomethicone (D = 4) | 13.20 |
| Surfactant (cyclomethicone and dimethicone copolyol) | 16.00 |
| Polyglyceryl 4-oleate | 0.50 |
| Pigment: | |
| Black and red iron oxide | 10.00 |
| Talc | 4.00 |
| Water | 46.00 |
| Sodium chloride | 2.00 |
| Propylene glycol | 8.00 |
| Methyl paraben | 0.20 |

*wherein the surfaces of the particles of pigment are chemically bonded to, and physically completely coated by, polymethyl hydrogen siloxane and mineral oil.*

14. [The composition of claim 6] *A cosmetic blusher that is a water-in-oil emulsion* having the formula

| | w/w % |
|---|---|
| cyclomethicone (D = 4) | 8.00 |
| Dimethicone (viscosity 10 cs) | 3.00 |
| Surfactant (cyclomethicone and dimethicone copolyol) | 18.00 |
| Laureth-9 | 0.50 |
| Propyl paraben | 0.10 |
| Pigment: | |
| D & C Red #7 Ca Lake | 1.00 |
| FD & C Yellow #5 Al Lake | .50 |
| Red iron oxide | 0.80 |
| Titanium dioxide | 2.00 |
| Talc | 9.70 |
| Water | 46.00 |
| Dimethicone copolyol | 0.20 |
| Sodium chloride | 2.00 |
| Propylene glycol | 8.00 |
| Methyl paraben | 0.20 |

*wherein the surfaces of the particles of pigment are chemically bonded to, and physically completely coated by, polymethyl hydrogen siloxane.*

15. [The composition of claim 6] *A cosmetic foundation that is a water-in-oil emulsion* having the formula

| | w/w % |
|---|---|
| cyclomethicone (D = 4) | 12.00 |
| Surfactant (cyclomethicone and dimethicone copolyol) | 20.00 |
| Phenyltrimethicone | 5.00 |
| Laureth-9 | 0.50 |
| Propyl paraben | 0.10 |
| Pigment: | |
| Red iron oxide | 0.90 |
| Yellow iron oxide | 1.75 |
| Black iron oxide | 0.22 |
| Talc | 3.33 |
| Titanium dioxide | 8.00 |
| Water | 39.00 |
| Sodium chloride | 1.00 |
| Propylene glycol | 8.00 |
| Methyl paraben | 0.20 |

*wherein the surfaces of the particles of pigment are chemically bonded to, and physically completely coated by, polymethyl hydrogen siloxane.*

\* \* \* \* \*